United States Patent
Chen et al.

(10) Patent No.: US 9,441,210 B2
(45) Date of Patent: Sep. 13, 2016

(54) METHOD OF REDUCING LEVELS OF URIC ACID

(71) Applicant: FOOD INDUSTRY RESEARCH AND DEVELOPMENT INSTITUTE, Hsinchu (TW)

(72) Inventors: Mei-Huei Chen, Hsinchu (TW); Siao-Jhen Chen, Hsinchu (TW); Hsun-Yin Hsu, Hsinchu (TW); Yen-Lin Chen, Hsinchu (TW); Kai-Ping Chen, Hsinchu (TW); Yi-Jen Yech, Hsinchu (TW); Li-Ting Wang, Hsinchu (TW); Hing-Yuen Chan, Hsinchu (TW)

(73) Assignee: FOOD INDUSTRY RESEARCH AND DEVELOPMENT INSTITUTE, Hsinchu (TW)

( * ) Notice: Subject to any disclaimer, the term of this patent is extended or adjusted under 35 U.S.C. 154(b) by 0 days.

(21) Appl. No.: 14/314,831

(22) Filed: Jun. 25, 2014

(65) Prior Publication Data

US 2015/0004150 A1 Jan. 1, 2015

Related U.S. Application Data

(60) Provisional application No. 61/839,686, filed on Jun. 26, 2013.

(51) Int. Cl.
*C12N 9/06* (2006.01)
*C12P 21/00* (2006.01)
*A61K 38/44* (2006.01)

(52) U.S. Cl.
CPC ............. *C12N 9/0048* (2013.01); *C12P 21/00* (2013.01); *A61K 38/44* (2013.01); *C12Y 107/03003* (2013.01)

(58) Field of Classification Search
None
See application file for complete search history.

(56) References Cited

U.S. PATENT DOCUMENTS

| | | |
|---|---|---|
| 3,475,276 A | 10/1969 | Kano et al. |
| 3,669,843 A | 6/1972 | Aunstrup et al. |
| 3,767,533 A | 10/1973 | Sugisaki et al. |
| 3,810,820 A | 5/1974 | Laboureur et al. |
| 4,062,731 A | 12/1977 | Snoke et al. |
| 4,882,280 A | 11/1989 | Takashio et al. |
| 4,987,076 A | 1/1991 | Takashio et al. |
| 5,660,603 A * | 8/1997 | Elliot ................ B01D 53/14  48/127.3 |
| 5,728,562 A | 3/1998 | Shigyo et al. |
| 5,955,336 A | 9/1999 | Shigyo et al. |
| 2010/0145116 A1* | 6/2010 | Van Keulen ............ C12P 23/00  585/23 |
| 2010/0151063 A1 | 6/2010 | Omori et al. |
| 2010/0316618 A1 | 12/2010 | Tsuboi et al. |
| 2011/0014168 A1 | 1/2011 | Tsuboi et al. |
| 2011/0195051 A1 | 8/2011 | Otero Casal et al. |

OTHER PUBLICATIONS

Difco & BBL Manual, 2nd Edition. Marine Agar 2216—Marine Broth 2216. [online], [retrieved on Jan. 7, 2016]. No date. Retrieved from the Internet <URL: https://www.bd.com/europe/regulatory/Assets/IFU/Difco__BBL/212185.pdf>.*
Office action issued on May 7, 2015 for the corresponding Taiwan, R.O.C. Patent Application No. 103122008.
Search report issued on May 7, 2015 for the corresponding Taiwan, R.O.C. Patent Application No. 103122008.
Pineiro-Vidal et al., "*Tenacibaculum discolor* sp. nov. and *Tenacibaculum gallaicum* sp. nov., isolated from sole (*Solea senegalensis*) and turbot (*Psetta maxima*) culture systems." International journal of systematic and evolutionary microbiology 58.1 (2008): 21-25.
Choi, Dong Han et al. "*Tenacibaculum litoreum* sp. nov., isolated from tidal flat sediment." Interational journal of systematic and evolutionary microbiology 56.3 (2006): 635-640.
Yasser R. Abdel-Fattah et al., Improved production of pseudomonas aeruginosa uricase by optimization of process parameters through statistical experimental designs, Process Biochemistry, 2005, pp. 1707-1714, vol. 40.
Mahmoud M. Nour El-Dein et al., Screening of Some Fungi for Uricolytic Activity, Quatar Univ. Sci. J., 1996, pp. 71-76, vol. 16(1).
Office action issued on Mar. 23, 2016 for the corresponding Taiwan, R.O.C. Patent Application No. 104142352.
Search report issued on Mar. 23, 2016 for the corresponding Taiwan, R.O.C. Patent Application No. 104142352.
English translation of the Office action issued on Mar. 23, 2016 for the corresponding Taiwan, R.O.C. Patent Application No. 104142352.
English translation of the Search report issued on Mar. 23, 2016 for the corresponding Taiwan, R.O.C. Patent Application No. 104142352.

\* cited by examiner

*Primary Examiner* — Renee Claytor
*Assistant Examiner* — Susan E Fernandez
(74) *Attorney, Agent, or Firm* — WPAT, P.C., Intellectual Property Attorneys; Anthony King

(57) ABSTRACT

The present invention relates to a method of reducing the level of uric acid in a subject, which comprises administering to said subject an effective amount of a fermentation product of *Tenacibaculum* sp. Also provided are a method of preventing and/or treating a disease or disorder related to hyperuricemia, a method of increasing the digestion of uric acid and a method of producing uricase.

4 Claims, 1 Drawing Sheet

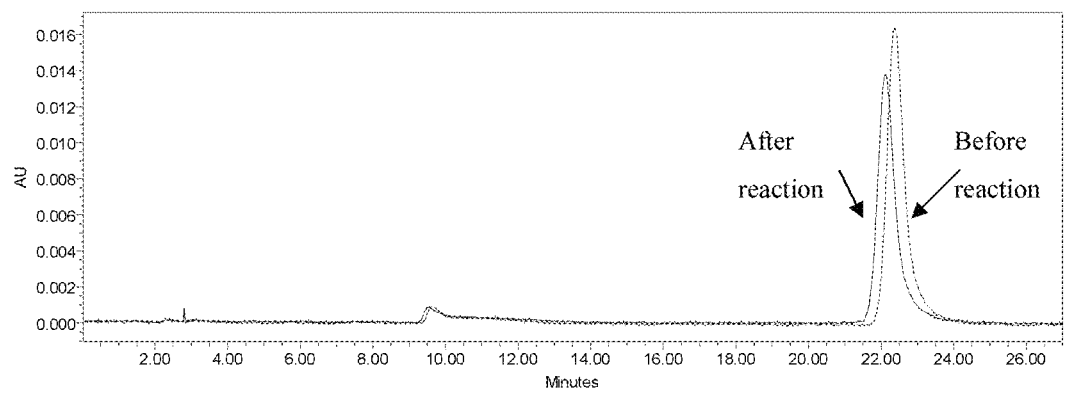

METHOD OF REDUCING LEVELS OF URIC ACID

FIELD OF THE INVENTION

The present invention relates to novel uses of marine bacteria. More particularly, the present invention relates to novel uses of *Tenacibaculum* sp. for lowering uric acid.

BACKGROUND OF THE INVENTION

Non-human mammals, such as rats and dogs, can produce uricase, which converts uric acid into micromolecular allantoin for excretion. Unlike the situation in other mammals, uric acid is the end product of purine metabolism in the human body. Therefore, when concentration of uric acid accumulated in blood is excessively high, hyperuricemia is caused.

Hyperuricemia is a common metabolic disorder, and can cause gout, hypertension, cardiovascular diseases, diabetes mellitus, and renal calculus, which may further lead to nephritis. According to a local epidemiological survey from 1993 to 2008, the prevalence of hyperuricemia is 21.6% in males and is 9.57% in females in Taiwan. At present, hyperuricemia cannot be cured through clinical treatment, but it has been proved that xanthine oxidase inhibitors and uricase are quite effective in reducing the level of uric acid in blood. Treatment of hyperuricemia is not covered by health insurance in Taiwan until symptoms arise. Consequently, health foods that can prevent hyperuricemia or alleviate its symptoms have gained popularity in the health food market.

At present, uricase is mainly produced by using organisms belonging to the genus *Aspergillus* sp. or *Bacillus* sp. U.S. Pat. No. 3,669,843 discloses that mutants of *Bacillus fastidiosus* (NCIB10423, 10424, 10425, 10372) are able to produce uricase when aerobically (220 rpm) cultured at 30° C. for 5 days. U.S. Pat. No. 3,810,820 discloses that bacteria such as *Streptomyces cellulosae*, *S. sulphureus*, *Bacillus megatherium*, *B. subtillus*, and *B. cereus*; yeast such as *Geotrichum candidum*, fungi such as *Aspergillus flavus*, *Asp. oryzae*, *Asp. tamarii*, *Asp. luchuensis*, *Asp. niger*, *Asp. sydowi*, *Asp. nidulans*, *Asp. wentii*, *Asp. fonsecaeus*, *Asp. clavatus*, *Asp. ustus*, *Asp. ochraceus*, *Penicillium frequentans*, *Pen. granulatum*, *Pen. griseum*, *Pen. canescens*, *Pen. spinulosum*, *Pen. thomii*, *Pen. waksmani*, *Pen. raistrickii*, *Pen. expansum*, *Pen. purpurescens*, *Pen. funiculosum*, *Pen. spiculisporum*, *Pen. velutinum*, *Pen. purpurogenum*, *Pen. spinulosum*, *Pen. lilacinum*, *Pen. rubrum*, *Cephalosporium* sp., *Alternaria tenuis*, *A. tenuis*, *Fusarium solani*, *Fus. moniliforme*, *Fus. coeruleum*, *Fus. oxysporum*, *Fus. orthoceras*, *Stemphylium macrosporoideum*, *Macrosporium apiospermum*, *Abisidia Glauca+*,*Mucor mucedo*, *M hiemalis*, *M racemosus*, *Rhizopus arrizus*, and *Basidiomycete* sp. are able to produce unease with average molecular weight of 93,000±3,000 when aerobically cultured with a suitable carbon source, nitrogen source, and uric acid. U.S. Pat. No. 4,987,076 indicates that *Bacillus* sp. TB-90 (FERM BP-795) is able to produce uricase with molecular weight of 120,000, in which enzyme activity can keep at pH 5 to 9 and 30° C. for 15 days, and the optimum temperature is 45° C. to 50° C. Such strains are also reported in U.S. Pat. No. 4,882,280 to produce uricase in a specific medium. U.S. Pat. No. 5,728,562 indicates that *Bacillus* sp. TB-90 is able to produce uricase with a specific sequence and molecular weight of 35,000, wherein the uricase is stable in a solution at pH 8.0 and 60° C. for 10 minutes. U.S. Pat. No. 5,955,336 also discloses that *Bacillus* sp. TB-90 (FERM BP-795) in a host cell of *Escherichia coli* such as JM109(pKOD316), JM109 (pKU1), ISW 1214(pEB2) is able to produce uricase with a specific sequence. U.S. Pat. No. 3,475,276 indicates that *Candida utilis* 6020 is able to produce uricase when cultured in a medium (5% glucose, 25% asparagine, 1% $K_2HPO_4$, 3% $MgSO_4$, 4%$(NH_4)_2SO_4$) containing uric acid, at pH at least 6.5 and at 15° C. to 35° C. for 8 to 24 hours. U.S. Pat. No. 3,767,533 indicates that novel *Corynebacterium uratoxidants* nov. sp. U-23(ATCC 21749), U-8(ATCC 21750), U-30(ATCC 21751), and U-31(ATCC 21752) are able to produce uricase when aerobically cultured at pH 5.5 to 9.0 and at 20° C. to 40° C. in the presence of 0.01% to 1.0% uric acid. U.S. Pat. No. 4,062,731 indicates that *Micrococcus luteus* NRRL B-8166 is able to produce high active uricase of about 1000 U/liter with average molecular weight of 93,000 dalton.

Fermentations and metabolic products are also reported. US 2010/0151063 indicates that barley fermented with fungi or yeast is able to reduce blood uric acid. US 2010/0316618 indicates that metabolic products of *Lactobacillus gasseri* strain OLL2922 (NITE BP-462) inhibits the increase of blood uric acid and can be used as food or pharmaceuticals. US 2011/0014168 indicates that *Lactobacillus gasseri* OLL2959(NITE BP-224) and *Lactobacillus oris* OLL2779 (NITE BP-22) are able to digest purine and further inhibit the increase of blood uric acid caused by diet.

However, contamination easily occurs when culturing the above mentioned microorganisms, which requires a long duration of fermentation. Thus, there is need for a novel method to reduce levels of uric acid.

SUMMARY OF THE INVENTION

One purpose of the present invention is to provide a method of reducing the level of uric acid in a subject, which comprises administering to said subject an effective amount of a fermentation product of *Tenacibaculum* sp.

Another purpose of the present invention is to provide a method of preventing and/or treating a disease or disorder related to hyperuricemia in a subject, which comprises administering to said subject an effective amount of a fermentation product of *Tenacibaculum* sp.

Another purpose of the present invention is to provide a method of increasing digestion of uric acid in a subject, which comprises administering to said subject an effective amount of a fermentation product of *Tenacibaculum* sp.

Another purpose of the present invention is to provide a method of producing uricase, comprising providing a fermentation product of *Tenacibaculum* sp. and obtaining uricase in the fermentation product of *Tenacibaculum* sp.

Another purpose of the present invention is to provide a composition comprising a fermentation product of *Tenacibaculum* sp.

BRIEF DESCRIPTION OF THE DRAWINGS

FIG. 1 is an HPLC chromatogram showing ability of strain 9B200 to digest uric acid.

DETAILED DESCRIPTION OF THE INVENTION

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the fermentation product of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each range are significant both in relation to and independently of the other endpoint. As used herein the term "about" refers to ±10%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural, and plural terms shall include the singular.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "*Tenacibaculum* sp." as used herein refers to microorganisms belonging to *Tenacibaculum* sp., such as *Tenacibaculum discolor*, *Tenacibaculum litoreum*, *Tenacibaculum mesophilum*, *Tenacibaculum litopenaei*, *Tenacibaculum adriaticum*, *Tenacibaculum aestuarii*, *Tenacibaculum amylolyticum*, *Tenacibaculum crassostreae*, *Tenacibaculum dicentrarchi*, *Tenacibaculum gallaicum*, *Tenacibaculum geojense*, *Tenacibaculum jejuense*, *Tenacibaculum lutimaris*, *Tenacibaculum maritimum*, *Tenacibaculum ovolyticum*, *Tenacibaculum skagerrakense*, *Tenacibaculum soleae*, and *Tenacibaculum aiptasiae*. The genus *Tenacibaculum* belongs to the family Flavobacteriaceae and *Tenacibaculum* sp. are gram-negative bacilli, and are heterotrophs that do not sporulate and have catalase and oxidase. Lacking flagella, *Tenacibaculum* sp. move in a gliding manner. They are heterotroph microorganisms that rely on oxygen. Menaquinone (MK-6) is a component in the major respiratory quinone of *Tenacibaculum* sp. Xanthophyl produced is mainly zeaxanthin without any Flexirubin-type pigment. The content of DNA G+C is in the range of 31 mol % to 33 mol %.

Preferably, *Tenacibaculum* sp. is selected from the group consisting of 09B200, 09B210, 09B219, 09B236, 09B374, 09B511, BCRC 17590, and BCRC 17655 obtained from FOOD INDUSTRY RESEARCH AND DEVELOPMENT INSTITUTE (NO. 331, SHIHPIN RD., HSINCHU CITY, TAIWAN, R.O.C.).

More preferably, *Tenacibaculum litoreum* 09B200 is deposited in the Deutsche Sammlung von Mikroorganismen und Zellkulturen (DSMZ) on Jun. 5, 2014, with accession number DSM 28895; *Tenacibaculum discolor* 09B210 is deposited in the Deutsche Sammlung von Mikroorganismen und Zellkulturen (DSMZ) on Jun. 5, 2014, with accession number DSM 28896. Deutsche Sammlung von Mikroorganismen und Zellkulturen (DSMZ) is located at Inhoffenstraβe 7B, 38124 Braunschweig, Germany.

The term "fermentation" as used herein denotes bulk growth of microorganisms on a growth medium.

The present invention provides a method of reducing the level of uric acid in a subject, which comprises administering to said subject an effective amount of a fermentation product of *Tenacibaculum* sp.

It was unexpected to find that the *Tenacibaculum* sp. of marine bacteria are able to reduce uric acid levels.

In one embodiment, the uric acid is included in an isolated sample. In another embodiment, the uric acid is presented in the subject. In one preferred embodiment of the invention, a fermentation product of *Tenacibaculum* sp. is able to reduce the level of uric acid in blood.

Manners of assaying the level of uric acid are known to artisans skilled in the field. In one preferred embodiment of the invention, the manner of assay is as described by Abdel-Fattah (Process Biochemistry, 2005, 40:1707-1714). Modifications of the assay can also be made as needed.

The manner of preparing the fermentation product of *Tenacibaculum* sp. can be any of those known to artisans skilled in this field or illustrated in the Examples. In one preferred embodiment of the invention, the fermentation is as described by Mahmoud (Qatar Univ. Sci. J., 1996, 16(1): 71-76). Modifications of the assay can also be made as needed. In one embodiment of the invention, the fermentation is aerobically culturing *Tenacibaculum* sp. The temperature of culturing ranges from about 15° C. to about 35° C.; preferably about 30° C. The medium is preferably PY broth (0.4% polypeptone, 0.2% yeast extract, 1% NaCl; pH 7.6) or PYG broth (0.4% polypeptone, 0.2% yeast extract, 0.5% glucose, 1% NaCl; pH 7.6). *Tenacibaculum* sp. mainly live in the ocean, so a culture medium containing seawater is optimal for growth of *Tenacibaculum* sp., but *Tenacibaculum* sp. may also grow in a culture medium containing NaCl at a concentration from 1% to 7% (w/v). Preferably, the fermentation product of *Tenacibaculum* sp. is prepared by culturing *Tenacibaculum* sp. in a medium containing about 1% to about 7% NaCl (w/v); preferably from about 2% to about 3%. In another aspect, because *Tenacibaculum* sp. is a marine bacteria, the fermentation product of *Tenacibaculum* sp. is preferably prepared by culturing *Tenacibaculum* sp. in a medium containing sea water. The concentration of the sea water in the medium is from about 1% to about 7% (v/v); preferably from about 1% to about 3.5% (v/v).

*Tenacibaculum* sp. needs to be cultured under a condition with appropriate concentration of sodium chloride. This reduces the possibility of bacterial contamination during fermentation and production, and allows its effectiveness in reducing uric acid levels to be achieved within a short duration of fermentation and culture.

Another purpose of the present invention is to provide a method of preventing and/or treating a disease or disorder related to hyperuricemia in a subject, which comprises administering to said subject an effective amount of a fermentation product of *Tenacibaculum* sp.

It has been shown that the fermentation product of *Tenacibaculum* sp. is effective in reducing uric acid levels in blood, and in preventing and/or treating a disease or disorder related to hyperuricemia. In one preferred embodiment of the invention, the disease or disorder related to hyperuricemia is selected from the group consisting of gout, hypertension, cardiovascular diseases, diabetes mellitus, renal calculus, and nephritis.

Another purpose of the present invention is to provide a method of increasing the digestion of uric acid in a subject, which comprises administering to said subject an effective amount of a fermentation product of *Tenacibaculum* sp.

It has been shown that the fermentation product of *Tenacibaculum* sp. is effective in reducing uric acid levels in blood, and in increasing digestion of uric acid.

Another purpose of the present invention is to provide a method of producing uricase comprising providing a fermentation product of *Tenacibaculum* sp. and obtaining uricase therein.

If strains of *Tenacibaculum* sp. are used to produce uricase, the possibility of bacterial contamination during fermentation and production can be reduced, and the uricase can be obtained within a short culture time. Therefore, organisms of *Tenacibaculum* sp. have potential value for being developed into strains for producing uricase.

The uricase produced can be further purified or provided in the form of a fermentation product. Manners of purifying uricase are known to artisans skilled in this field.

Another purpose of the present invention is to provide a composition comprising a fermentation product of *Tenacibaculum* sp.

The composition according to the invention can be a food composition or a pharmaceutical composition.

The fermentation product of *Tenacibaculum* sp. can be added to a conventional food composition (i.e. an edible food or drink or precursors thereof) in the manufacturing process of the food composition. Almost all food compositions can be supplemented with the fish skin fermentation product of the invention. Food compositions that can be supplemented with the fish skin fermentation product of the invention include, but are not limited to, candies, baked goods, ice creams, dairy products, sweet and savory snacks, snack bars, meal replacement products, fast foods, soups, pastas, noodles, canned foods, frozen foods, dried foods, refrigerated foods, oils and fats, baby foods, or soft foods painted on breads, or mixtures thereof.

The fermentation product of *Tenacibaculum* sp. of the invention can be formulated with a pharmaceutically or cosmetically acceptable carrier and/or an excipient. As used herein, "carrier" or "excipient" refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The pharmaceutical composition of the invention can be administered topically or systemically by any method known in the art, including, but not limited to intramuscular, intradermal, intravenous, subcutaneous, intraperitoneal, intranasal, oral, mucosal or external routes. In the present invention, depending on the route of administration, the pharmaceutical composition and cosmetic composition can be formulated into various forms, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof.

The following examples are provided to aid those skilled in the art in practicing the present invention.

EXAMPLES

Example 1

*Tenacibaculum* sp. Able to Reduce Amount of Uric Acid

Eight strains, 09B200, 09B210, 09B219, 09B236, 09B374, 09B511, BCRC 17590, and BCRC 17655, were cultured on a plate of marine medium at 30° C. for 2 to 5 days. Then, referring to an improvement of the method of Mahmoud, et al. (1996), one transferring loop of bacteria was transferred and added to 0.5 ml water agar solution (0.2% water agar+0.05% Tween 80), and the solution was plated on a plate of marine medium containing 0.1% uric acid (MUA). After 3 to 7-day culturing at 30° C., sizes of transparent rings produced through uricolysis by the eight marine strains were observed. The results show that all the test strains have ability to reduce the level of uric acid (Table 1).

TABLE 1

Ability of eight strains of *Tenacibaculum* sp. to reduce amount of uric acid of in MUA plate

| Strain No. | Microorganism | Colony diameter (mm) | Transparent ring diameter (mm)[a] |
|---|---|---|---|
| 09B200 | *Tenacibaculum litoreum* | 9.84 | 24.38 |
| 09B210 | *Tenacibaculum discolor* | 9.35 | 30.36 |
| 09B219 | *Tenacibaculum litoreum* | 9.74 | 28.02 |
| 09B236 | *Tenacibaculum aiptasiae* | 10.59 | 16.36 |
| 09B374 | *Tenacibaculum discolor* | 13.03 | 40.51 |
| 09B511 | *Tenacibaculum mesophilum* | 9.21 | 19.52 |
| BCRC 17590 | *Tenacibaculum litopenaei* | 6.49 | 27.58 |
| BCRC 17655 | *Tenacibaculum aiptasiae* | 4.96 | 16.15 |

[a]including the size of strains

Example 2

Liquid State Fermentation

Eight strains, 09B200, 09B210, 09B219, 09B236, 09B374, 09B511, BCRC 17590, and BCRC 17655, were cultured on a plate of marine medium at 30° C. for 2 to 5 days. Then, 7 ml sterile water was added, and a transferring loop was used to scrape the bacteria and uniformly mix the bacteria with the sterile water, so as to obtain a bacterial suspension. An 1 ml bacterial suspension was taken and added to a 250 ml conical flask containing 50 ml PY culture solution (0.4% polypeptone, 0.2 yeast extract, and 1% NaCl; pH 7.6) or PYG culture solution (0.4% polypeptone, 0.2 yeast extract, 0.5% glucose, and 1% NaCl; pH 7.6), and subjected to shaking fermentation for 3 and 7 days at 30° C. and 150 rpm, to obtain the fermentation products.

Example 3

Amount of Uricase

High-speed centrifugation (10,000 rpm, 10 minutes) was performed on the ferments of the eight strains in Example 2, to obtain fermentation supernatants. By adopting an improvement of the method of Abdel-Fattah, et al. (2005), 200 μl 200 μM uric acid solution (50 mM sodium phosphate butter; pH 7.4) was added to a 96UV-well plate, 10 μl fermentation supernatant was then added, and a light absorption value (a) at $OD_{290}$ was measured. After reaction for 30 minutes at 30° C., a light absorption value (b) at $OD_{290}$ was measured. An appropriate amount of standard urate oxidase (250U Uricase, Sigma) was weighted and dissolved in an appropriate amount of sodium phosphate buffer (pH 7.4). The resulting solution was diluted into solutions of concentrations of 5 mU/ml, 10 mU/ml, 25 mU/ml, 50 mU/ml, 75 mU/ml, and 100 mU/ml, so as to make a calibration curve. An absorbance (a-b) of the samples was obtained through measurement, and the content of uric acid was calculated by using an interpolation method. Results show that after 3 to 7-day culturing in two culture solutions (PY and PYG), six *Tenacibaculum* sp. marine strains had the ability to produce uricase.

TABLE 2

The unease amount produced by six *Tenacibaculum* sp. bacteria fermented in PY and PYG for 3 and 7 days

| | | Uricase (mU/ml) | | | |
|---|---|---|---|---|---|
| | | PY | | PYG | |
| Strain No. | Microorganism | 3 day | 7 day | 3 day | 7 day |
| 09B200 | *Tenacibaculum litoreum* | 14.60 | 10.35 | 9.80 | 5.41 |
| 09B210 | *Tenacibaculum discolor* | 22.88 | 31.30 | 32.15 | 22.05 |
| 09B219 | *Tenacibaculum litoreum* | 14.91 | 11.17 | 19.23 | 7.74 |
| 09B236 | *Tenacibaculum aiptasiae* | 10.66 | 4.66 | 8.55 | 4.78 |
| 09B374 | *Tenacibaculum discolor* | 25.07 | 31.12 | 31.59 | 21.50 |
| 09B511 | *Tenacibaculum mesophilum* | — | 3.47 | — | 18.07 |

Example 4

Assay of Uricase

Sterile water was respectively added to the six strains in Example 1, and for each strain, a transferring loop was used to scrape the bacteria, so as to obtain a bacterial suspension. After centrifugation (4,000 rpm, 15 minutes), wet bacteria were obtained by removing the supernatant. 1 g wet weight of biomass was taken and added to 10 ml uric acid solution (50 μg/ml), and then the uric acid solution was shaken for one minute, 30° C. reaction for one hour and was filtered through a 0.22 μm filter membrane for HPLC analysis. Results are shown in Table 3.

TABLE 3

Amount of uric acid digested by six *Tenacibaculum* sp. bacteria

| Strain No. | Microorganism | Amount of uric acid before reaction (μg/ml) | Amount of uric acid after reaction for 1 hour (μg/ml) | Rate of digestion of uric acid (μg/hr · g wet weight) |
|---|---|---|---|---|
| 09B200 | *Tenacibaculum litoreum* | 18.400 | 15.463 | 29.37 |
| 09B210 | *Tenacibaculum discolor* | 16.979 | 15.843 | 11.36 |
| 09B219 | *Tenacibaculum litoreum* | 16.368 | 16.075 | 2.93 |
| 09B236 | *Tenacibaculum aiptasiae* | 16.116 | 15.561 | 5.55 |

TABLE 3-continued

Amount of uric acid digested by six *Tenacibaculum* sp. bacteria

| Strain No. | Microorganism | Amount of uric acid before reaction (μg/ml) | Amount of uric acid after reaction for 1 hour (μg/ml) | Rate of digestion of uric acid (μg/hr · g wet weight) |
|---|---|---|---|---|
| 09B374 | *Tenacibaculum discolor* | 17.052 | 16.682 | 3.70 |
| 09B511 | *Tenacibaculum mesophilum* | 18.036 | 16.975 | 10.61 |

FIG. 1 is an HPLC chromatogram showing ability of strain 09B200 to digest uric acid.

Conditions of HPLC analysis: the separation column is Amide (XBridge™ Amide, 3.5 μm particle size) manufactured by Waters Corporation, USA; elution solvent: ammonium acetate (10 mM, pH 5.0)/acetonitrile=10:90 (v/v); flow rate: 1.2 mL/min; detection wavelength: photo-diodarray spectrophotometer 290 nm (Waters); injection volume: 10 μl.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method of producing uricase comprising providing a fermentation product of *Tenacibaculum* sp. and purifying uricase from the fermentation product of *Tenacibaculum* sp.

2. The method according to claim 1, wherein the *Tenacibaculum* sp. is selected from the group consisting of 09B200 and 09B210.

3. The method according to claim 1, wherein the fermentation product of *Tenacibaculum* sp. is prepared by culturing *Tenacibaculum* sp. in a medium containing about 1% to about 7% NaCl (w/v).

4. The method according to claim 1, wherein the fermentation product of *Tenacibaculum* sp. is prepared by culturing *Tenacibaculum* sp. in a medium containing sea water.

* * * * *